United States Patent [19]

Franetzki

[11] 4,217,894

[45] Aug. 19, 1980

[54] APPARATUS FOR SUPPLYING MEDICATION TO THE HUMAN OR ANIMAL BODY

[75] Inventor: Manfred Franetzki, Uttenreuth, Fed. Rep. of Germany

[73] Assignee: Siemens Aktiengesellschaft, Berlin & Munich, Fed. Rep. of Germany

[21] Appl. No.: 902,810

[22] Filed: May 4, 1978

[30] Foreign Application Priority Data

May 13, 1977 [DE] Fed. Rep. of Germany ....... 2721752

[51] Int. Cl.² .............. A61J 7/00; A61M 7/00; A61M 31/00
[52] U.S. Cl. .................. 128/213 R; 128/214 F; 128/260
[58] Field of Search ............ 128/213, 214 F, 215, 128/260

[56] References Cited

U.S. PATENT DOCUMENTS

| 3,732,865 | 5/1973 | Higuchi et al. | 128/260 |
| 3,760,804 | 9/1973 | Higuchi et al. | 128/260 |
| 3,760,805 | 9/1973 | Higuchi | 128/260 |
| 3,797,492 | 3/1974 | Place | 128/214 F X |
| 3,894,538 | 7/1975 | Richter | 128/260 |
| 3,896,806 | 7/1975 | Wichterle | 128/260 |
| 3,995,632 | 12/1976 | Nakano et al. | 128/260 |
| 4,077,405 | 3/1978 | Haerten et al. | 128/214 F |
| 4,140,122 | 2/1979 | Kühl et al. | 128/260 |

*Primary Examiner*—Henry K. Artis
*Attorney, Agent, or Firm*—Hill, Van Santen, Steadman, Chiara & Simpson

[57] ABSTRACT

In the illustrated embodiments, medication is stored in an implantable housing in solid form, and solvent is supplied to the solid medication to form the infusion fluid as needed for maintaining the desired dosage rate. The rate of supply of solvent may be controlled to insure a saturated solution of the medication under all operating conditions. The solvent may be the local bodily fluid which enters the housing via a semipermeable membrane, or a sealed solvent reservoir may be provided within the housing.

20 Claims, 2 Drawing Figures

4,217,894

APPARATUS FOR SUPPLYING MEDICATION TO THE HUMAN OR ANIMAL BODY

BACKGROUND OF THE INVENTION

The invention relates to an apparatus for supplying medication to the human or animal body, comprising a reservoir for the medication and a conveyance and dosing unit for transporting the medication from the reservoir to a discharge port. The apparatus can be implanted in the body or worn externally on the body.

Apparatus for supplying medication which can be worn on the body of a patient and, in particular, which is suitable for implantation in the body of the patient, should be as small and lightweight as possible. A major demand is also that the medication filled into the reservoir have a sufficiently long stability period in order to achieve refill intervals for the medication which are as long as possible. Apparatus of the type initially cited is known wherein a supply of the liquid medication is stored in high concentration and smallest volumes of the liquid medication are continuously transported, dosed by the reservoir, by a conveyance and dosing unit to the opening of a discharge catheter. However, such apparatus is only suitable for medications which are sufficiently soluble in a liquid which can be tolerated by the body and which are also sufficiently stable over a long period in contact with the apparatus materials at body temperature. In the case of many medications, such as, in particular, insulin, heparin and other polypeptides, however, only relatively low degrees of solubility are manifest and/or stability problems occur at high concentrations. In apparatus for medications of this type, the refill interval for the liquid medication is hence relatively short and there is an overall restriction in the applied use of the apparatus on the patient. Furthermore, in the case of apparatus having a larger supply of liquid medication in the reservoir, there is always the danger that, in case of error, the entire fluid medication will leak out of the reservoir into the patient's body. An overdose of medication such as this, particularly in the case of the administering of insulin during diabetes therapy, can result in severe harm to the patient.

SUMMARY OF THE INVENTION

Accordingly, it is the object of the invention to realize an apparatus for the supply of medication to the human or animal body, in the reservoir of which it is possible to store larger quantities of medication without incurring the risk of leakage of the liquid medication.

The object is inventively achieved by virtue of the fact that the medication is stored in the reservoir in a solid form, and that a solvent is capable of being supplied to the solid medication for the purpose of dissolving the solid medication to an infusion fluid which can be discharged by the conveyance and dosing unit via the exit port. Preferably, body fluid can be used as the solvent for the solid medication, which body fluid is drawn to the solid medication by the conveyance and dosing unit in a predeterminable dose via a semipermeable membrane in the apparatus housing. In another embodiment of the invention, a special fluid is used as the solvent of the solid medication which is stored in an additional reservoir which preferably has a refill opening in the apparatus housing.

The apparatus in accordance with the invention proceeds from the fact that in solid form, the majority of medications are stable for long periods of time, and manifests a minimum solubility in a body-compatible liquid; particularly, in water. Thus, by means of a complete dissolution of the solid medication only directly prior to its being discharged into the patient's body, the disadvantageous stability problems of the liquid medications having high concentration in the case of the known infusion apparatus do not occur. In the apparatus according to the invention, the solid medication can be stored in a sufficient amount in the reservoir in an amorphous or crystalline state for the entire time of applied use of the apparatus on the patient. The transcutaneous refilling of medication in the case of the implanted apparatus is thereby completely avoided. In the apparatus in accordance with the invention, the solvent flows around the solid medication for a sufficiently long period of time until the solution has reached a state of complete saturation. The saturated solution is then released into the body in measured doses. The flow which is induced by the pump simultaneously defines the rate of release of the medication, since the solubility is essentially constant given the minimal body temperature fluctuations.

Further details and advantages of the invention will be apparent from the following description of sample embodiments in conjunction with the accompanying sheet of drawings; other objects, features and advantages will be apparent from this detailed disclosure and from the appended claims.

DETAILED DESCRIPTION

Figure 1:
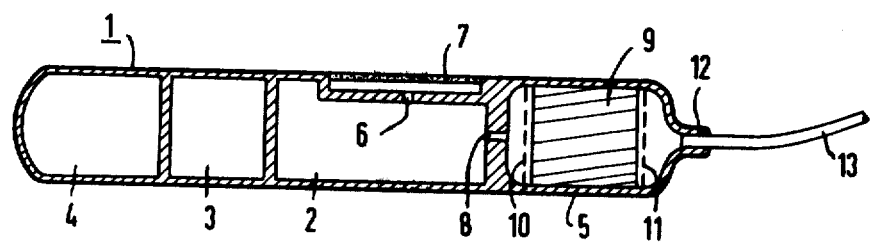
FIG. 1 is a longitudinal sectional view illustrating a first sample embodiment wherein body fluid is drawn (or suctioned) in by means of a pump.

In FIG. 1, reference numeral 1 designates a housing in which a pump 2, as the delivery and dosing unit, units 3 and 4 for control circuits and energy supply (battery), and a reservoir 5 for the medication are located. Pump 2 is connected via a conduit 6 with a large-area, semipermeable membrane 7 in the housing wall. It can be useful to envelop an absorbent wick, which is placed in the patient's body, with the semipermeable membrane 7, in order to increase the absorption surface for the body fluid. The semi-permeable membrane 7 and/or the wick advantageously have hydrophilic properties. Via semipermeable membrane 7, which is formed from such a material that only low molecular substances, preferably molecules up to a size of those of water, are allowed to pass through, body fluid is drawn in from the vicinity of the apparatus and conveyed via conduit 8 to reservoir 5. In reservoir 5, there is disposed a block 9 of solid medication which can fill the entire reservoir 5. On both sides of the block, there are arranged close-meshed filters. The infusion fluid saturated with medication reaches the discharge port 12 of housing 1 at which a catheter 13 is arranged.

Figure 2:
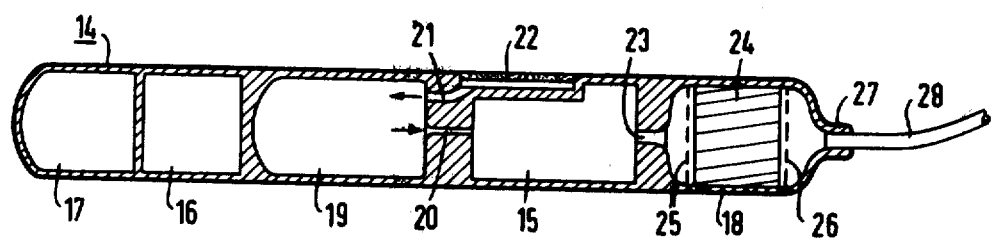
FIG. 2 is a sectional view showing a second sample embodiment wherein an additional reservoir for a solvent is present.

In FIG. 2, the housing of the apparatus is designated with 14, which, in turn, comprises a pump 15, units 16 and 17 for control and energy supply (battery) and a reservoir 18 for the solid medication. In addition, an additional reservoir 19 for the solvent is arranged in the housing 14 which is connected with pump 15 via conduit 20. Via an additional conduit 21, reservoir 19 is connected to a refill adapter 22 in the apparatus housing. The solvent is conveyed from receptacle 19 via conduit 20 and a conduit 23 to reservoir 18 in which the medication block 24 is disposed. On both sides of medication block 24, there are again arranged close (or narrow) meshed filters 25 and 26. A catheter 28 is connected to the discharge 27 of housing 14.

The apparatus housings 1 and 14 are formed from a material capable of implantation such as high-grade steel or titanium. Preferably, housings 1 and 14 will form flat capsules of the type used for heart-pacemaker housings which are readily capable of being introduced in the patient's body. The medication blocks 9 and 24 in the reservoirs 5 and 18 of the illustrated apparatus are to manifest as large a surface as possible in order to guarantee a sufficiently long contact period of the solvent with the medication and, in this manner, produce a fully saturated infusion fluid. This is achieved by virtue of the fact that block 9 or 24, which fills out the entire volume of the reservoir 5, or 18, respectively, is constructed to be porous and has continuous channels passing through the entire block from the inlet to the outlet side thereof. In the case of a crystalline medication, this condition is already satisfied by compressing the individual crystallites. The close-meshed filters 10, 11, or 25, 26, prevent a floating away of small solid medication particles which can be separated by the solvent from the entire block. Preferably suitable as the conveyance and dosing unit 2, or 15, respectively, are cylinder pumps with stepping motor drive or also an electro-osmotic pump, as already described in detail in the patent literature.

The apparatus according to the sample embodiment described in FIG. 1 can be of the smallest possible construction. It is particularly suited for implantation in the patient's body. An apparatus according to the sample embodiment described in FIG. 2 is suited for an optional construction of an apparatus capable of implantation or capable of being worn externally on the body of the patient. In this apparatus, solvents other than water can also be employed. This can be of advantage if the medication, for example, is not soluble in body fluid or water, if reactions with the body fluid can take place, or if an additional opening of the apparatus housing leading to the body is to be avoided. Nevertheless, the advantages remain as compared with the apparatus of the prior art wherein liquid medication is stored in a reservoir. The solid medication is likewise dissolved only directly prior to discharge into the patient's body and, as a consequence, only a short term contact of the dissolved medication with the apparatus material will take place. Thus, the long term stability of the medication fluid is not a necessary secondary requirement. Moreover, in the apparatus in accordance with the invention, the same amount of solvent lasts longer than in the case of the apparatus of the prior art, since solutions generally are stable over a long period of time only when reliably far from saturation. Thus, in the apparatus according to the sample embodiment of FIG. 2, correspondingly more medication will be conveyed per unit of volume of fluid because of the higher solute concentration which is feasible. In addition, the refilling of solvent is less dangerous than the refilling of a medication solution. Whereas this is entirely unproblematic in the case of an apparatus worn externally on the patient's body, in the case of an implanted apparatus, during the transcutaneous refilling of fluid, the conditions are also more readily controllable than in the case of the apparatus of state of the art. It is easier to keep the solvent sterile than a medication fluid. Also, the solvent can be selected to be of such a body compatible nature that, in the case of error, the fluid leaking out will not present any danger to the patient. In the latter case, even during a spontaneous discharge of the entire fluid, the solvent will not even be entirely saturated with medication.

The inventive apparatus can also be supplemented to form an adaptively controlled or self-regulating apparatus by means of selection of a suitable controlled variable, such as, for example, the blood sugar concentration. In this instance, the supply of the medication is no longer controlled by a program which is input in the apparatus in the form of a program transmitter (or generator), or controlled externally by means of remote control; but on the contrary, the supply of the medication is controlled by a special sensor with an associated control system and nominal (setpoint) value input. Additional sensors, for example for temperature, are also conceivable which can take into account the increasing solubility of the solvent for the medication at higher temperatures.

The pump 2 has its intake side connected to conduit 6 and its output side supplying pure solvent to conduit 8. The pump 15 is similarly connected between conduits 20 and 23. Each pump 2, 15 may comprise a stricture or roller pump operated by a step motor. The step motor and stricture pump have already been described in the patent literature. Alternatively, each pump 2, 15 can be an electro-osmotic pump such as shown in U.S. Pat. No. 3,894,538 issued July 15, 1975.

The pump control 3, 16 for the step motor may correspond to that given in German Offenlegungsschrift 25 13 467 (U.S. Ser. No. 669,459) and the rate of the step pulse generator may be controlled from a temperature sensor (such as 21) so as to correct the transport rate or capacity of the pump 2, 15 in accordance with the temperature-dependent solubility curve of the solvent for the solid medication 9, 24. Thus the pump 2, 15 operates at a rate such that a fully saturated solution results at all transport rates of the pump 2, 15, regardless of variations in body temperature.

It will be apparent that many modifications and variatons may be effected without departing from the scope of the novel concepts and teachings of the present invention.

I claim as my invention:

1. Apparatus for the infusion of medical fluids into the human or animal body, comprising in combination:
   a storage receptacle having reservoir means providing a reservoir (5, 18) with a fluid inlet (8, 23) providing a fluid passage leading to said reservoir (5, 18) and with a discharge port (12, 27) providing a fluid passage leading from said reservoir (5, 15),
   a solid medication (9, 24) disposed in said reservoir (5, 18) such that the fluid inlet (8, 23) provides a fluid passage in fluid communication with said solid medication,
   a conveyance and dosing unit in fluid communication with said fluid inlet (8, 23) comprising supplying means for the supply of a solvent to said solid medication (9, 24) via the fluid passage provided by said fluid inlet such that the solvent progressively dissolves the solid medication to form a medical fluid in the vicinity of said solid medication in said reservoir,
   said storage receptacle being constructed to accommodate supply of said medical fluid so formed in said reservoir (5, 15), to said discharge port (12, 27), while retaining in said reservoir undissolved portions of said solid medication, and said conveyance and dosing unit being operable to control the dose of said medical fluid supplied to said discharge port by controlling the transport of solvent to said reservoir whereby in the storage receptacle the amount of solid medication dissolved per dose of medical fluid corresponds to a desired dosing schedule.

2. Apparatus according to claim 1, characterized in said supplying means for the solvent comprising a semipermeable membrane (7) having its exterior side in communication with the body fluid of the body receiving the medication and having its interior side communicating with said reservoir means (5, 18) for the supply of the body fluid to the reservoir means as solvent for dissolving the solid medication in said reservoir means.

3. Apparatus according to claim 2, characterized in said semipermeable membrane (7) being permeable only to low-molecular substances of molecular size not substantially exceeding the molecular size of the water molecule.

4. Apparatus according to claim 1, characterized in the supplying means for supplying the solvent comprising an absorptive wick disposed in fluid communication with the body fluid of the body receiving the medication.

5. Apparatus according to claim 2 or 3, characterized in the supplying means for supplying the solvent comprising material with hydrophilic properties in fluid communication with the body fluid of the body receiving the medication.

6. Apparatus according to claim 1 with the solvent supplying means for supplying the solvent comprising an additional reservoir (19) for storing the solvent and for supplying the solvent to said reservoir means (18) for the purpose of dissolving the solid medication (24).

7. Apparatus according to claim 1, characterized in that the reservoir means contains an amount of said solid medication (9, 24) coordinated with the flow of the solvent thereto such that a fully saturated solution results for all rates of transport of the medication by the conveyance and dosing unit (2, 15).

8. Apparatus according to claim 1, characterized in the reservoir means (5,18) containing a block of the solid medication (9, 24) and being constructed to provide at least one through-flow channel for the solvent so that the solvent flows through the block of solid medication during operation of the apparatus.

9. Apparatus according to claim 8, characterized in the block of said solid medication (9, 24) with its entire volume in the reservoir means (5, 18) being porous to the solvent.

10. Apparatus according to claim 8, characterized in fine-meshed filter means (10, 11; 25, 26) confining the solid medication for the purpose of preventing the flow of undissolved particles of the solid medication (9, 24) to the discharge port (12, 27).

11. Apparatus according to claim 1, characterized in that the conveyance and dosing unit (2, 15) comprises pump means having its inlet side connected with the solvent supplying means (7, 19) and having its output side connected with said reservoir means (5, 18), said pump means being operated at a rate such that a fully saturated solution is supplied to said discharge port (12, 27).

12. Apparatus according to claim 11, characterized in said pump means comprising a stricture pump.

13. Apparatus according to claim 11 characterized in said pump means for the solvent comprising an electro-osmotic pump.

14. Apparatus according to claim 1, characterized in an apparatus housing (1, 14) containing said reservoir means and said conveyance and dosing unit and having a cathether (13, 28) arranged at said discharge port (12, 27).

15. Apparatus according to claim 11, characterized in a temperature sensor means controlling said pump means (2, 15) for correcting the conveying capacity of the pump means in accordance with the temperature-dependent solubility curve of the solvent for the solid medication (9, 24).

16. A medication supply system according to claim 1 with said reservoir means (5, 18) having said solid medication (9, 24) therein, and confining means (10, 11; 25, 26) for confining solid particles from the solid medication against flow to said discharge port (12, 27) while accommodating flow of medication when dissolved in said solvent to said discharge port.

17. A medication supply system according to claim 16, with said medication supply means having means operable for supplying a substantially saturated solution of the medication to said discharge port (12, 27) under all operating conditions of said infusion apparatus.

18. A medication supply system according to claim 16, with said solvent supply means comprising means (7) for communication with ambient body fluid of the body receiving the medication and for supplying such ambient body fluid to said reservoir means (5) as the solvent for dissolving the solid medication.

19. A medication supply system according to claim 17 with said solvent supply means comprising means (19) for storing said solvent for supply to said reservoir means (18) for dissolving the solid medication.

20. A medication supply system according to claim 16 with an implantable housing containing said reservoir means and said solvent supply means.

* * * * *